(12) United States Patent
Sleefe et al.

(10) Patent No.: US 6,369,588 B1
(45) Date of Patent: Apr. 9, 2002

(54) SENSOR SYSTEM FOR WEB INSPECTION

(76) Inventors: Gerard E. Sleefe, 1 Snowcap Ct., Cedar Crest, NM (US) 87008; Thomas J. Rudnick, 626 E. Jackson Rd., St. Louis, MO (US) 63119; James L. Novak, 11048 Malaguena La. NE., Albuquerque, NM (US) 87111

(*) Notice: Subject to any disclaimer, the term of this patent is extended or adjusted under 35 U.S.C. 154(b) by 0 days.

(21) Appl. No.: 09/437,350

(22) Filed: Nov. 9, 1999

(51) Int. Cl.[7] .......................... G01B 7/04; G01N 27/22; G01R 27/26
(52) U.S. Cl. .................. 324/686; 324/663; 324/671
(58) Field of Search ................ 324/663, 671, 324/686, 687

(56) References Cited

U.S. PATENT DOCUMENTS

| | | | |
|---|---|---|---|
| 3,827,809 A | 8/1974 | Nash | 356/200 |
| 4,422,035 A | 12/1983 | Risko | 324/61 P |
| 4,450,404 A * | 5/1984 | Williams et al. | 324/226 |
| 4,455,039 A | 6/1984 | Weitzen et al. | 283/83 |
| 4,482,860 A | 11/1984 | Risko | 324/61 P |
| 4,634,917 A | 1/1987 | Dvorsky et al. | 310/328 |
| 4,766,389 A | 8/1988 | Rhoades et al. | 324/61 QS |
| 4,891,584 A * | 1/1990 | Kamieniecki et al. | 324/752 |
| 5,138,268 A | 8/1992 | Mulkey et al. | 324/671 |
| 5,223,797 A * | 6/1993 | Mayer et al. | 324/688 |
| 5,270,664 A * | 12/1993 | McMurtry et al. | 324/690 |
| 5,281,921 A | 1/1994 | Novak et al. | 324/671 |
| 5,315,232 A | 5/1994 | Stewart | 324/72 |
| 5,378,994 A | 1/1995 | Novak et al. | 324/671 |
| 5,473,257 A | 12/1995 | Novak et al. | 324/671 |
| 5,537,048 A | 7/1996 | Novak | 324/690 |
| 5,602,486 A | 2/1997 | Novak | 324/671 |
| 5,742,167 A * | 4/1998 | Haynes | 324/671 |
| 5,928,475 A * | 7/1999 | Chase et al. | 324/664 X |
| 6,087,584 A * | 7/2000 | Chase | 324/693 |

OTHER PUBLICATIONS

Sleefe, Peglow & Hamrick, The application of unattended ground sensors to stationary targets, SAND97–0970C (date unavailable).

Ivan Kadar, Signal Processing, Sensor Fusion, and Target Recognition VII—13–15 Apr. 1998, vol. 3374, pp. 495–504.

* cited by examiner

Primary Examiner—Glenn W. Brown
(74) Attorney, Agent, or Firm—Geroge H Libman (57) ABSTRACT

A system for electrically measuring variations over a flexible web has a capacitive sensor including spaced electrically conductive, transmit and receive electrodes mounted on a flexible substrate. The sensor is held against a flexible web with sufficient force to deflect the path of the web, which moves relative to the sensor.

22 Claims, 7 Drawing Sheets

SENSOR SYSTEM FOR WEB INSPECTION

The United States Government has rights in this invention pursuant to Department of Energy Contract No. DE-AC04-94AL85000 with Sandia Corporation.

BACKGROUND OF THE INVENTION

This invention relates to the measurement of defects in the construction of flexible web material, and more particularly to the measurement of defects in greige (pronounced 'gray') goods; fabrics in their raw state, typically, right from the loom.

Many products are manufactured most efficiently in continuous processes that produce long sections of flat material in which the length and width are much larger than the thickness. Continuous webs of materials, including plastic sheet, paper, floor coverings, tire plies and textiles, are typically made into rolls and cut to length after the bulk of the manufacturing processes are performed. Typically, a series of value-adding operations such as drying, pressing, tinting, curing, printing and coating are performed at multiple processing stations.

Because each processing stage adds value, the work-in-progress increases in value as it moves down the production line. It is therefore desirable to inspect the output of each stage both to eliminate adding downstream value to unrepairable product and to provide feedback control to the previous stage. For example, if greige goods at the output of a loom are detected as having a large section with missing threads, the problem may be corrected before a significant additional amount of faulty cloth is woven.

Figure 7:
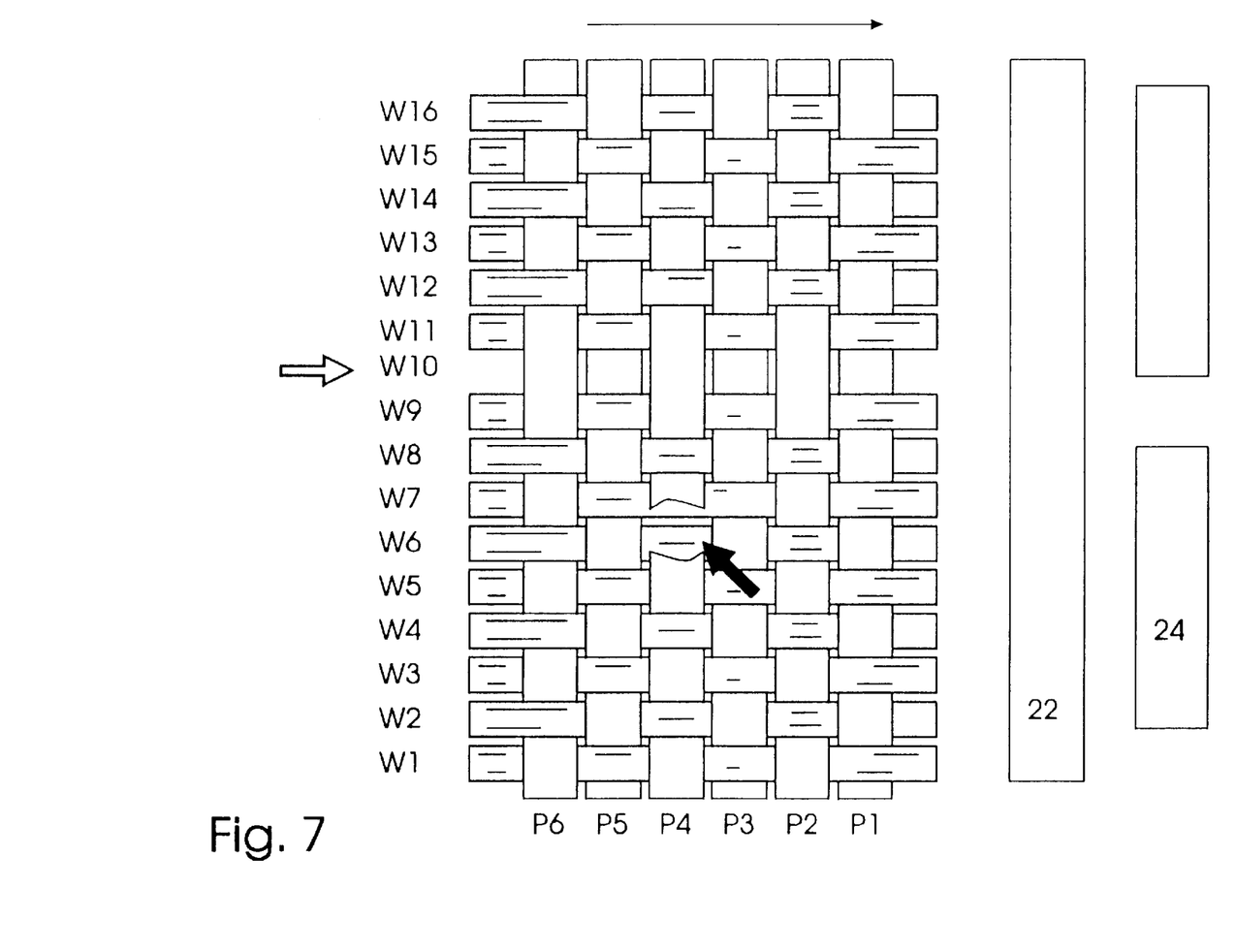
FIG. 7 shows a top view of a woven web approaching the sensor.

The greige goods to be inspected are woven threads in sheets of various widths, some about 70" wide. As shown in FIG. 7, two axes of threads are interlaced together at right angles; the warp threads W run the length of the goods, the pick threads P are woven above and below adjacent warp threads across the goods. The woven cloths have a specified number of ends per inch, generally in the range of 40 to 200 epi. The threads vary in diameter, but are often about 10 mils, and are comprised of even smaller fibers spun together. These fibers are either natural fibers, like cotton, or synthetics like polyester. Both natural and synthetic fibers are dielectrics with relative permittivities greater than 1. The spun fibers enclose some air so that the resulting thread is made up of a combination of fiber particles and air, resulting in the thread having an effective relative permittivity of only a little more than 1.

In a production setting, greige goods move in the direction of the warp threads at speeds on the order of 300 to 1200 picks per minute.

Capacitance sensing is a promising technique for measuring parameters on sheet or web materials. U.S. Pat. No. 5,281,921 of J. Novak et al. describes a system where various parameters of sheet material, such as edge smoothness and weld thickness, are measured by the change in capacitance between two spaced electrodes in proximity to the system under test. U.S. Pat. No. 5,537,048 of J. Novak described a roller apparatus for measuring the impedance of web materials containing conductive wires that passed over the roller.

Capacitance sensors can measure either the offset of the sensor from a conductive workpiece or the permittivity of a dielectric workpiece that is in contact with the sensor. Great difficulties arise when attempting other types of measurements with capacitance sensors. They are not suited for inspecting the interior of metals or for looking through metals. If used to inspect dielectric materials that are not in contact with the sensor, a change in offset will produce the same type of sensor response as a change in dielectric constant. Thus, strict offset control is necessary to ensure reliable data.

Any pair of conductors forms a capacitor, and that capacitance is the ratio of the charge to the voltage across the conductors. The capacitance of a pair of conductors is determined by their geometry and by all the media surrounding them. Any variation in the surrounding media (such as variations in the thread thickness and distribution for greige goods) will cause a variation in the measured capacitance. In general, capacitances are either measured or are calculated from computer boundary value or finite element models, as simpler mathematical models provide only estimates of actual capacitances since they generally ignore fringing fields.

Figure 1:
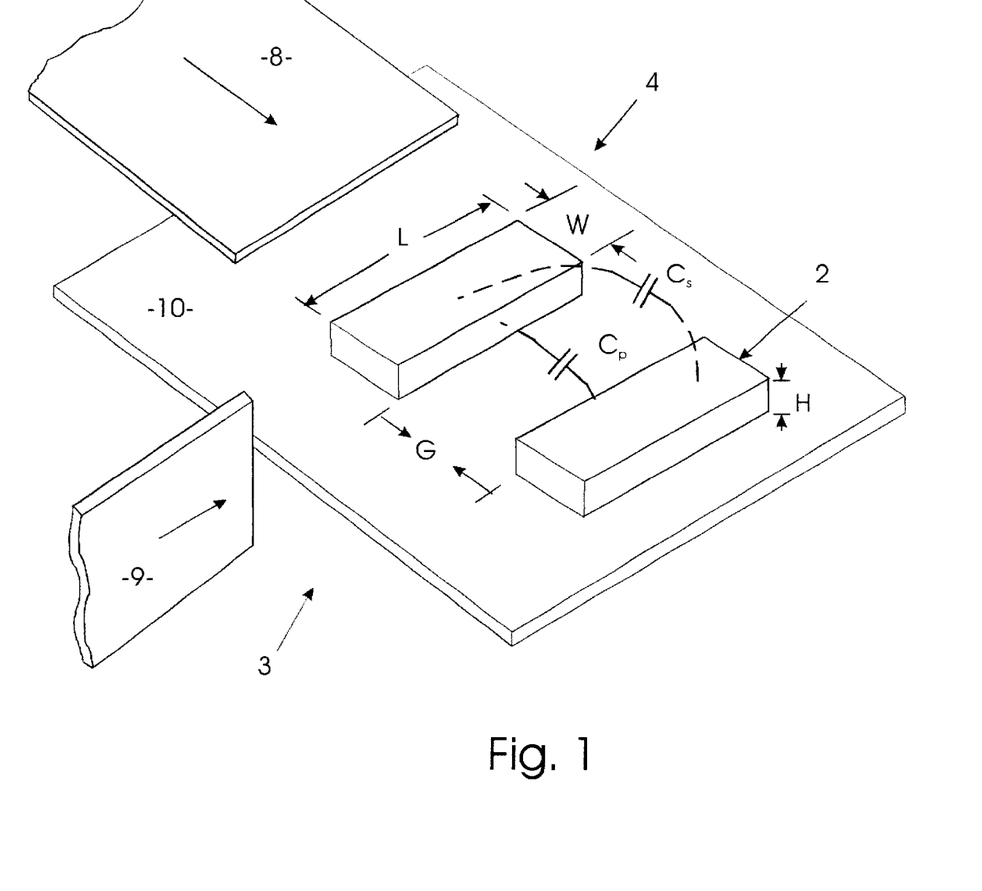
FIG. 1 shows the capacitive fields between two adjacent metal plates.

FIG. 1 shows the two conductors 2, 4 of a capacitor to be metal plates, of length L, height H, and width W. Two common arrangements of capacitor plates that are easily realizable using printed wiring board technology are aligned parallel plates or coplanar plates, although a variety of other arrangements exist. For any such capacitor, the capacitance is the sum of the direct ($C_p$) and fringing field contributions ($C_f$).

The direct contribution for the aligned parallel plate case, assuming a uniform medium between the plates with dielectric constant $\epsilon$, is approximated to be $$C_p = \varepsilon \frac{LH}{G} \tag{1}$$

where G is the gap or separation. This contribution is due to all the field lines starting on one plate and ending on the other that are constrained to the volume immediately between the two plates and are perpendicular to the plates. The fringing field contribution is due to all the field lines that are not constrained to the volume immediately between the plates. If the value of H is large compared to G, then the fringing contribution is small compared to the direct contribution. For such a case, the height of the plates and the dielectric constant outside the plates plays a very small role in determining the total capacitance.

Such an arrangement (parallel plates) would make a useful sensor only if the material 9 to be inspected were placed between the plates and acted as the dielectric of the capacitor. This setup can be called a two-sided measurement because electronic components must be placed on both sides of the material. A two-sided measurement can be very sensitive but also requires a complicated mechanical mount.

Alternatively, the coplanar plate arrangement (with parallel lengths L) can be used to make a one-sided measurement of a material 8 that is a fixed distance above the plates. For this case, the capacitance is again the sum of the direct and fringing field contributions. Here, however, the direct contribution is made purposely small since H<<G making $C_p$ approach zero. Thus, for this geometry, the fringing field capacitance becomes the dominant term. For a printed wiring board, metal thicknesses are usually on the order a few mils but the fringing field contribution remains about as large as it was in the parallel plate case. Thus, it now contributes a larger share of the total capacitance resulting in a sensor that is very sensitive to changes in the fringing field.

The fringing field contribution can be treated as two parts: the first part is above the plates and the second part is below the plates. If the plates are conductors on the top side of a circuit board, then the second part can be contained inside the circuit board by proper grounding of a metallization layer covering the other side of the circuit board, and its contribution can be controlled and kept constant. The first part is determined by the dielectric material 8 above the plates and by any conductive material in close proximity. By placing a dielectric material in contact with the plates or at a fixed offset, and by removing any conductive material close to the plates, the change in capacitance between the plates will be almost entirely determined by the change in dielectric constant of the dielectric material.

If conductive material is placed in close proximity to the plates, then either of two effects will occur depending on whether the conductive material is ac-grounded or not. If the material is ungrounded, then field lines from the driving plate will excite the material, which will reradiate and enhance the capacitance between the plates. If the material is grounded, then field lines from the driving plate will be shunted to ground, and the capacitance between the plates is reduced. Similarly, use of a ground plane on the printed circuit board layer immediately below the plates will minimize the backside capacitance.

SUMMARY OF THE INVENTION

It is an object of this invention to provide a coplanar electrode arrangement on a flexible circuit board that is curved to conform to the path of the material.

It is another object of the invention to provide a system for detecting defects in a web of material passing over coplanar sensors.

To achieve the foregoing and other objects, and in accordance with the purpose of the present invention, as embodied and broadly described herein, the present invention may comprise a system for electrically measuring variations over a flexible web comprising a web support structure; a flexible web affixed to the web support structure and extending under longitudinal tension along a path extending from a first end to a second end; and a capacitive sensor comprising a dielectric support having rigidly mounted thereon spaced, electrically conductive, transmit and receive electrodes. A sensor support rigidly holds a portion of the dielectric support against said web with sufficient force to cause the path to be longer than the shortest distance between the first and second ends, the electrodes being adjacent the dielectric support. The web moves relative to the sensor.

Additional objects, advantages, and novel features of the invention will become apparent to those skilled in the art upon examination of the following description or may be learned by practice of the invention. The objects and advantages of the invention may be realized and attained as particularly pointed out in the appended claims.

BRIEF DESCRIPTION OF THE DRAWINGS

The accompanying drawings, which are incorporated in and form part of the specification, illustrate an embodiment of the present invention and, together with the description, serve to explain the principles of the invention.

DETAILED DESCRIPTION OF THE INVENTION

Figure 2:
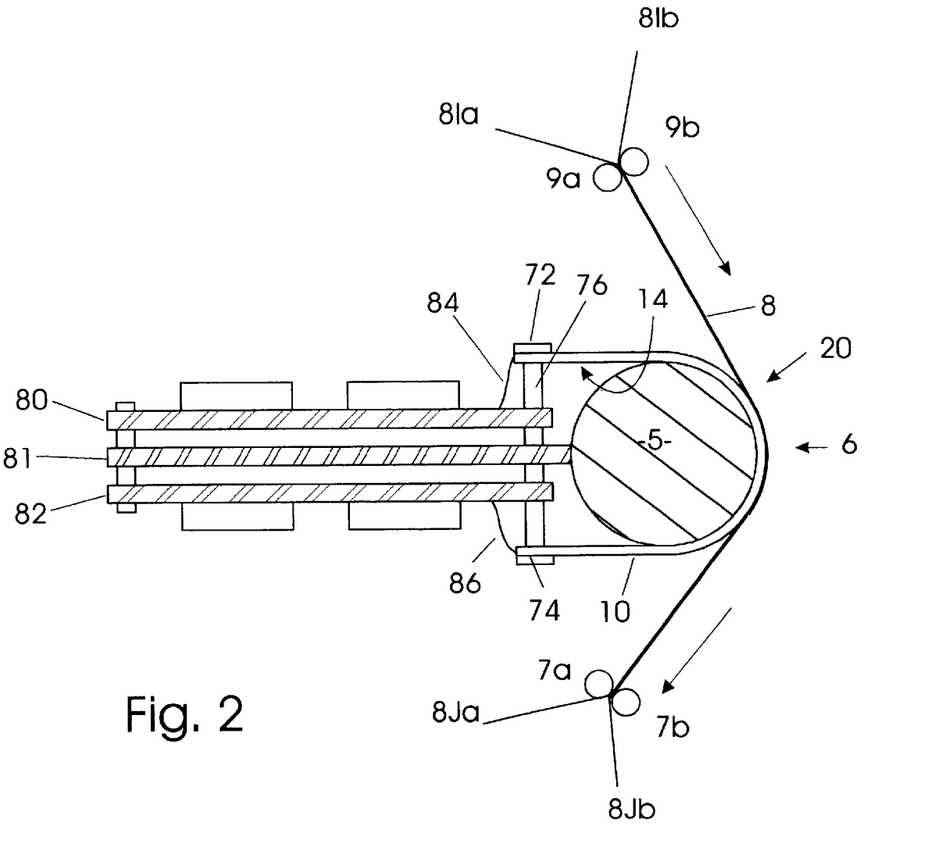
FIG. 2 shows a sensor in contact with a web and a cross section view of the circuit board of the invention.

In accordance with this invention, and as shown in FIG. 2, a flexible web 8 (viewed on edge) has a width extending into the figure and a length extending under longitudinal tension from one end 8I to opposing end 8J, which ends 8I and 8J are supported and guided by a supporting structure in a manner well known in the art. In the preferred embodiment, web 8 moves along a path extending from 8Ia or 8Ib to a guide 9, to a guide 7, and to 8Ja or 8Jb. Guides 9 and 7 may comprise any bearing surface which applies a force normal to the surface of web 8 such as a roller or fixed bar. The number and location of guides 9 depends on the path of web 8. A guide 9a is used if the end of web 8 is located at 8Ia, while a guide 9b is used if the end is at 8Ib.

This invention contemplates the capacitive measurement of variations in web 8 at a location between guides 9 and 7, which guides define the ends of the portion of web 8 being measured. In prior art capacitive systems, the sensor head would be placed adjacent web 8 as it follows the straight line path between guides 9 and 7. Such embodiments have difficulty caused by slight lateral movement of web 8 relative to the sensor. Accordingly, as shown in FIG. 2, this invention utilizes sensor 3 rigidly mounted such that an outer surface 6 of sensor 3 forms a bearing surface over which web 8 passes at a location which is not on the shortest distance between guides 9 and 7. As disclosed hereinafter, the capacitive sensor is adjacent surface 6. Since web 8 is maintained in tight contact with surface 6 because of the tension in web 8, lateral movement of web 8 relative to sensor 3 is eliminated.

Although the preferred embodiment shows web 8 moving from end 8I over sensor 3 to end 8J, it should be understood by those skilled in the art that this part of the invention also contemplates web 8 being held stationary and having sensor 3 moved along web 8. And while the particular sensor 3 discussed hereinafter is a preferred embodiment, other sensors having bearing surface 6 over which web 8 passes may also be used in the practice of the invention.

As discussed below, a preferred embodiment of capacitive sensor 3 includes a spaced pair of conductors formed as plates 2, 4 of FIG. 1, rigidly mounted with respect to each other on a structure such as flexible circuit board 10.

Figure 3:
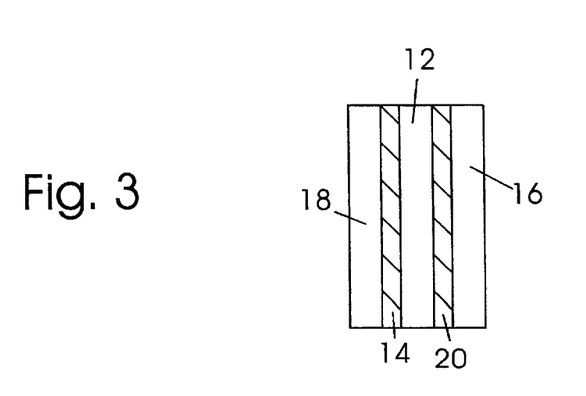
FIG. 3 shows a cross section of the circuit board of the sensor of FIG. 2
Figure 4:
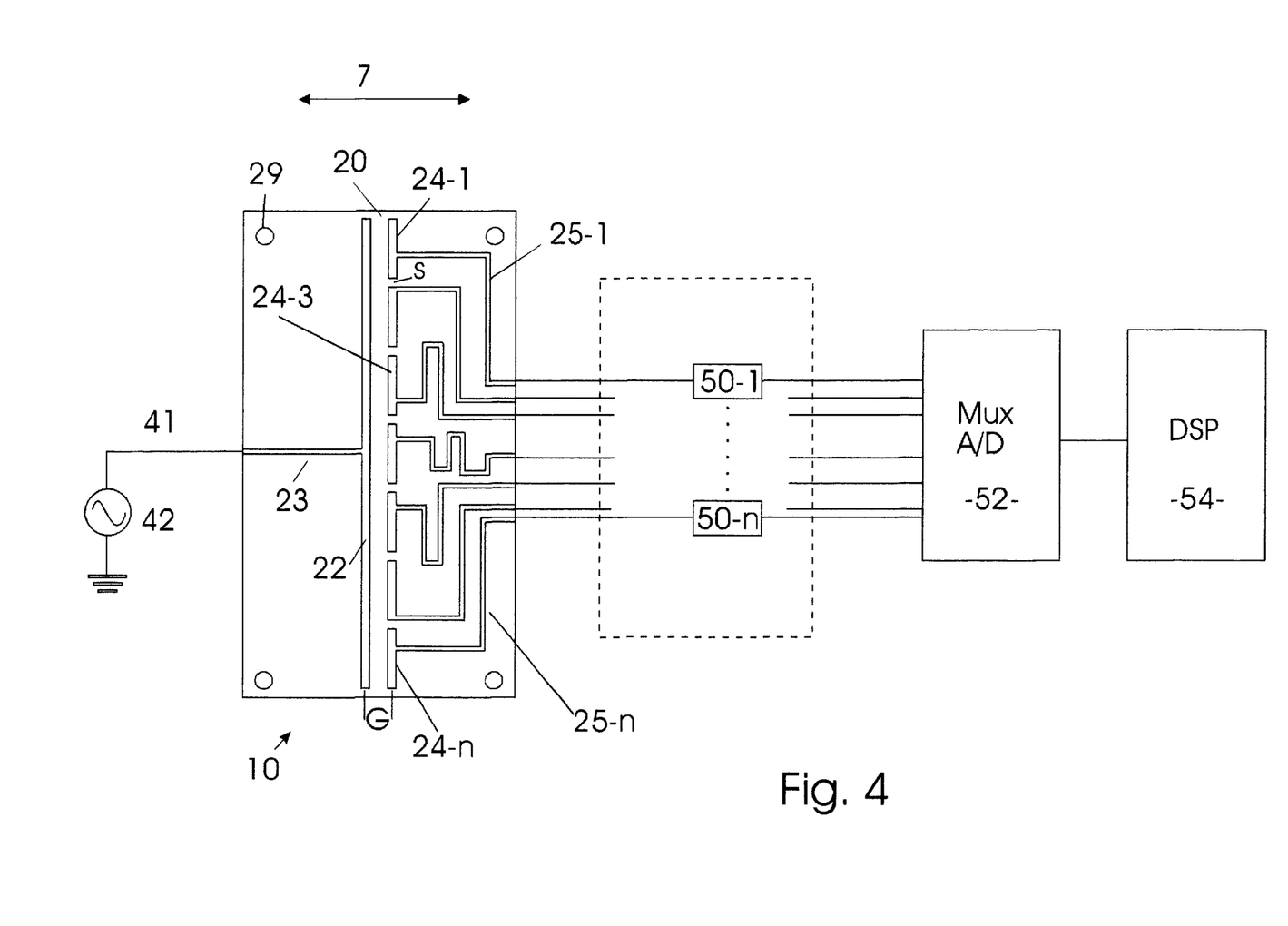
FIG. 4 shows a top view of the circuit board of FIG. 3 and associated circuitry.

FIGS. 3 and 4 show a flexible circuit board 10 made of a thin flexible dielectric material 12 having coated on one side there of a thin conductive coating 14 and on the opposing side thereof an opposing thin conductive coating that has been patterned using conventional printed circuit board techniques into a pattern 20. A thin flexible dielectric protective coating 16 covers conductive pattern 20, while an opposing thin flexible dielectric protective coating 18 preferably covers conductive coating 14.

In a preferred embodiment of the invention, layer 12 consists of a 2 mil (0.002 inch) layer of a thin polyamide film (Kapton™, E.I. du Pont de Nemours and Company) which is known for excellent tear and abrasion resistance and is conventionally used for flexible circuit boards. Layer 14 and pattern 20 consist of 1 ounce/ft² copper which typically has a thickness (H in FIG. 1) of about 1.4 mils. Each of bottom layer 18 and cover layer 16 consists of an additional layer of Kapton, and the thickness of cover layer 16 should be as thin as feasible. One mil was used in the preferred embodiment. Other materials and thicknesses could be used for the components of circuit board 10 consistent with the teachings of this invention.

FIG. 4 shows pattern 20 on layer 12 with cover layer 16 removed. As shown in FIG. 4, pattern 20 preferably includes an elongated rectangular transmit electrode 22 that extends for approximately the length of board 10 perpendicular to the direction of motion of web 8 (represented by arrow 7). Electrode 22 corresponds to plate 2 of FIG. 1. A conductive transmit trace 23 extends from electrode 22 to an edge of board 10 where it is connected through an external electrical connection such as wire 41 to the output of an oscillator 42 in a manner well known in the art.

Pattern 20 further includes a plurality of spaced receive electrodes 24-(1), 24-(2), . . . 24-(n) aligned parallel to and spaced from transmit electrode 22 by a gap G. Each rectangular receive electrode 24-(x), where x=1 to n, corresponds to electrode 4 of FIG. 1 and has a length L and a width W, and is aligned end-to-end with and separated from its neighbor electrode 24-(x+1) by a distance S. Each receive electrode 24-(x) is also electrically connected to an edge of board 10 by a conductive trace 25-(x). Preferably, each trace 25-(x) is laid out in a meandering path or the like so that the length (and characteristic impedance) of all such traces is approximately the same value. The design of such traces is a routine matter for those of ordinary skill in circuit board design. The free end of each trace 25-(x) is connected to a corresponding analog circuit 50-(x) (each sensor 24 connects to its individual analog circuit 50), an A/D converter 52, and a microprocessor 54, as discussed hereinafter.

The aforementioned components should be compactly mounted in a manner that enables the invention to be readily utilized to monitor a web in an existing manufacturing location. Such a configuration is shown in FIG. 2, where flexible circuit board 10 has been curved around and fastened to a metal guide bar 5 over which web 8 passes as part of its normal processing cycle. Circuit board 10 is arranged with transmit electrode 22 and receive electrodes 24-(x) parallel to the axis of bar 5 (or perpendicular to the direction of movement of web 8) and on the outer (convex) side of circuit board 10. In order to ensure good contact with web 8, the electrodes are placed adjacent a point c on the surface of bar 5 over which web 8 is completely in contact with bar 5. For the example shown in FIG. 2, point c may be located anywhere within the bracket indicated on the figure.

As shown in FIGS. 2 and 4, circuit board 10 has been fastened to bar 5 by a plurality of screws 72 (one is shown in FIG. 2) extending through holes 29 (FIG. 4) in circuit board 10 and fastened with nuts 74. The electronics (discussed hereinafter) are contained on rigid circuit boards 80–82 which are held in stack relationship by screw 72 and spacer sleeves 76 surrounding screw 72. Middle circuit board 81 extends tightly against bar 5 and serves to fasten the assembly in position on bar 5. Electrical connections between flexible circuit board 10 and rigid circuit boards 80–82 is via ribbon conductors 84, 86. The layout of the electronic components on rigid circuit boards 80–82 is a routine design matter for one of ordinary skill in the art.

Many other structures for connecting flexible circuit board 10 to bar 5 are also contemplated in the practice of this invention. For example, wedges or other structure could be provided on the inside surface of flexible board 10 to assist in holding it against bar 5. The electronic components could also be mounted on extensions of flexible circuit board 10 instead of rigid boards 80–82; alternatively, rigid boards 80 and 82 could be soldered or otherwise electrically connected directly to the ends of flexible board 10. For this invention, the important teaching is that the transmit and receive electrodes are on a flexible circuit board that is fastened over bar 5 at a position where the web will make good contact as part of its regular path of movement; the exact manner in which board 10 is fastened to bar 5 is not a significant factor.

The remaining questions for the sensor design for a particular application are (1) how to choose the plate parameters L, H, W, S and G; (2) how to determine parasitic elements; (3) what effects these parasitics cause; and (4) how to lay out the circuit board.

The first and second questions may be answered through computer modeling. Two-dimensional boundary value solution modeling was used to evaluate sensitivity versus geometry for the coplanar plate case. Also calculated were parasitic terms. These calculations were done after a ground plane was inserted into the model, as it would be on the bottom layer of the circuit boards, and as discussed above. The parameter L, which would be along the pick axis of the woven cloth, was not used in the computer model. Instead, the model assumed an infinite length in that direction. So the sensor length versus sensitivity issue needs to be discussed separately.

Figure 5:
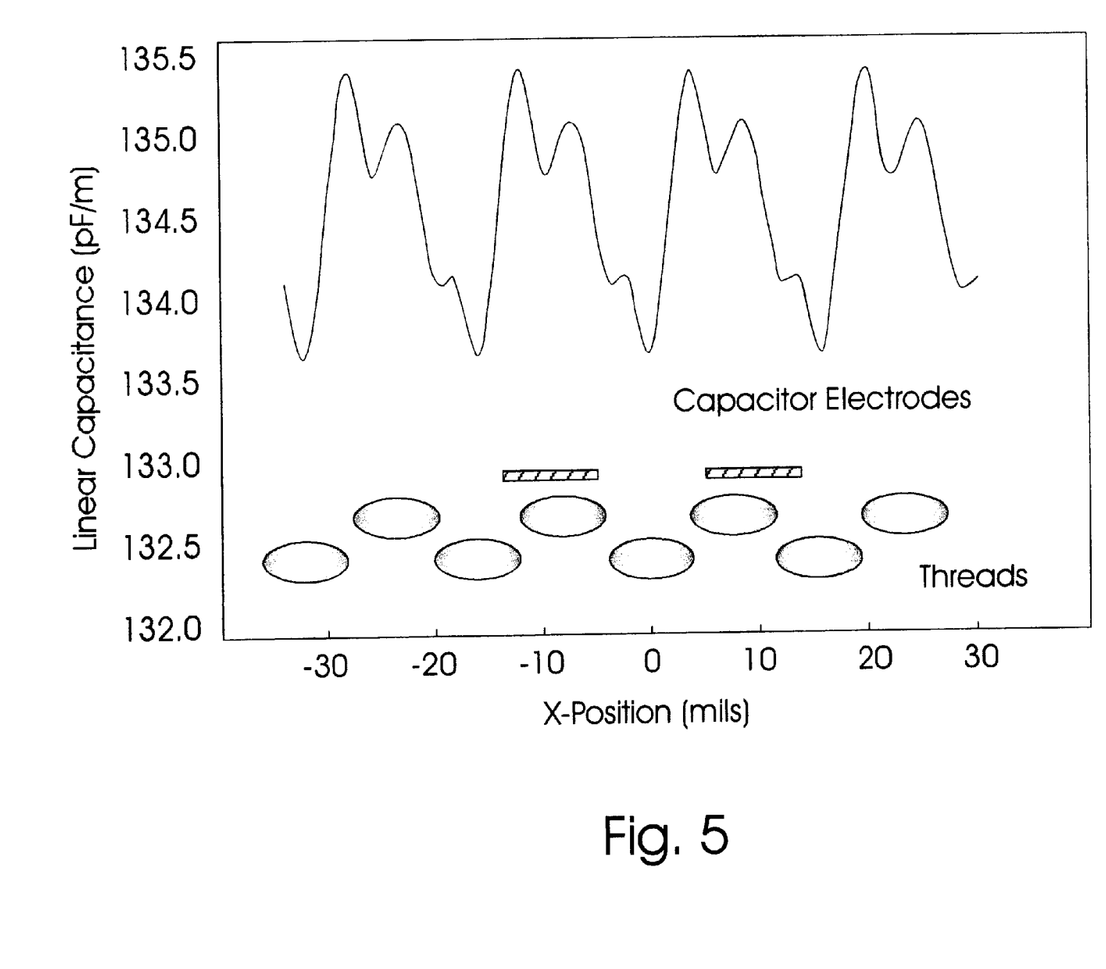
FIG. 5 shows calculated capacitance changes as a function of thread position for the sensor of FIG. 4.

FIG. 5 was created with ELECTRO™ (Integrated Engineering Software, Inc., Winnipeg, Canada), an electrostatic analysis program that shows a plot of the calculated linear capacitance of the illustrated capacitor electrodes (which electrodes extend infinitely into the page) as the pair is moved over the thread pattern shown. It is seen that the maximum capacitance occurs when the center of the capacitor gap is located at the left-hand edge of the upper thread. (The pick threads P are illustrated; the warp threads W which lie in the direction of movement are not illustrated in this figure.) This finding is not intuitively obvious since one would expect the capacitance to be a symmetrical function around the electrodes for a symmetrical field distribution. However, the design of the charge amplifier (as discussed hereinafter) clamps the right-hand electrode at virtual ground distributing the electric field uniformly over that electrode. The surface charges on the left-hand electrode are not uniformly distributed since the oscillator drives that electrode to a potential and hence the field is not uniformly distributed. Thus, the overall field pattern is not symmetrical around the electrodes resulting in a non-symmetrical sensitivity to the threads. The non-sinusoidal nature of the capacitance is understood to be due to the spatial convolution of electric field with multiple threads. The ELECTRO simulations also showed that the capacitive coupling peaked when the electrode gap was approximately equal to the thread spacing.

The computer modeling results indicate that the sensitivity to individual threads peaked when the plate gap, G, was equal to the spacing between threads. Since thread counts vary widely, different pad gaps need to be designed for different thread counts for best sensitivity. However, a given pad gap can successfully image a range of thread counts.

A second result is that the plate width, W, acts as an aperture on the measurement. Wider plates increase the depth into the material that the capacitor senses but also distribute local details. Narrower plates have finer definition but do not measure deeply buried flaws in the material. A pad width of approximately twice the thread diameter provides a good compromise between the two effects. As such, pad width for woven cloth should be approximately 20 mils.

The plate height H is determined by processing characteristics and, for a typical 1 ounce/ft² copper board, is equal to 1.4 mils. The values of the parasitic capacitances to ground are easily approximated by Equation 1. Parasitic impedances may be reduced by thinning and shortening traces on the circuit board and by increasing the board thickness.

The sensor length is determined by warp resolution concerns. Typically, several warp ends will fall under a sensor element. Measurement of the DC voltage from the sensor can be used to infer missing or extra warp ends, such as the missing thread at position W10 of FIG. 7, indicated by the white arrow. The length of the sensor ultimately determines the warp flaw sensitivity. Let $N_w$ equal the number of warp ends per inch. Aligned with the pick axis, a sensor of length L allows $N_w L$ warp ends to cross it. As L increases, the sensitivity to a defect in a single warp end decreases.

The third sensor design question can also be answered through computer modeling. PSPICE™ (MicroSim Corp., Irvine, Calif.) models confirmed that large parasitic capacitances the sensor pickup electrode 24 and ground cause a significant decrease in the upper cut-off frequency of the charge amplifier circuit. Large parasitic capacitances to ground cause a premature roll-off in circuit sensitivity since they appear in parallel to the sensor capacitor but are shunted to ground. Thus, the larger the parasitic capacitance, the more signal current is shunted to ground and the lower the gain in the charge amplifier. Inattention to this design rule will cause an increase in thermal sensitivity of the charge amplifier. Parasitic values above 100 pF will raise the 3 dB cutoff above 100 kHz. Since the oscillator used in the circuit operates at approximately 50 kHz, this can reduce the sensor sensitivity. A 3" long, 24 mil wide trace on a 2 mil thick Kapton board will create a 33 pF parasitic term.

The function of the analog circuitry 50-x is to convert the capacitance of the sensor plates 22, 24-(x) to an easily readable voltage signal. Complicating factors are that the 0.1 pF sensor capacitance value is extremely small and that the input capacitance of most integrated circuits and the parasitic capacitance from circuit traces are often over 50 times larger than the sensor value. A third complication is that these systems are often operated in an electrically noisy environment.

Measurements of the sensor capacitance can be made at any frequency, but very low and very high frequency measurements introduce significant difficulties. In general, the current through a capacitor is given by $$I_c = C\frac{dV}{dt} + V\frac{dC}{dt} \qquad (2)$$

where $I_c$ is the capacitor current, C is the capacitance, and V is the voltage across the capacitor. For most applications, C is a constant and the second term of Eq. 2 is zero. However, for this invention, the information desired from this sensor is contained in the term dC/dt.

If a DC bias is placed across the sensor, dV/dt=0 and a signal current is only produced when the capacitance changes. Additionally, large signals are only produced when the capacitance changes quickly. On a greige loom, cloth is produced rather slowly with threads passing by the sensor at a slow rate resulting in a small dC/dt and a subsequently small current. It is obvious that a DC measurement would be loom speed dependent, which is undesirable. Thus, exciting the sensor with an oscillator input at an intermediate frequency provides circuit design advantages since the current into the charge amplifier is a sum of both the signal due to the oscillator and the signal due to the cloth.

The qualities that make an oscillator 42 a good choice for capacitance sensing are low distortion, large amplitude, and high stability. High amplitude stability is of prime importance since the signal is an amplitude-modulated signal on top of a carrier signal, and any drift in the oscillator amplitude would be seen detected as a cloth flaw. Frequency drift is not usually of significant concern since the input bandwidth of the detector circuits is generally large compared to the frequency drift.

A preferred embodiment uses an oscillator 42 operating at an oscillation frequency of approximately 50 kHz and about a $2V_{p-p}$ output swing. It was implemented utilizing an XR-8083A precision waveform generator from EXAR Corporation, Fremont, Calif.

Figure 6A:
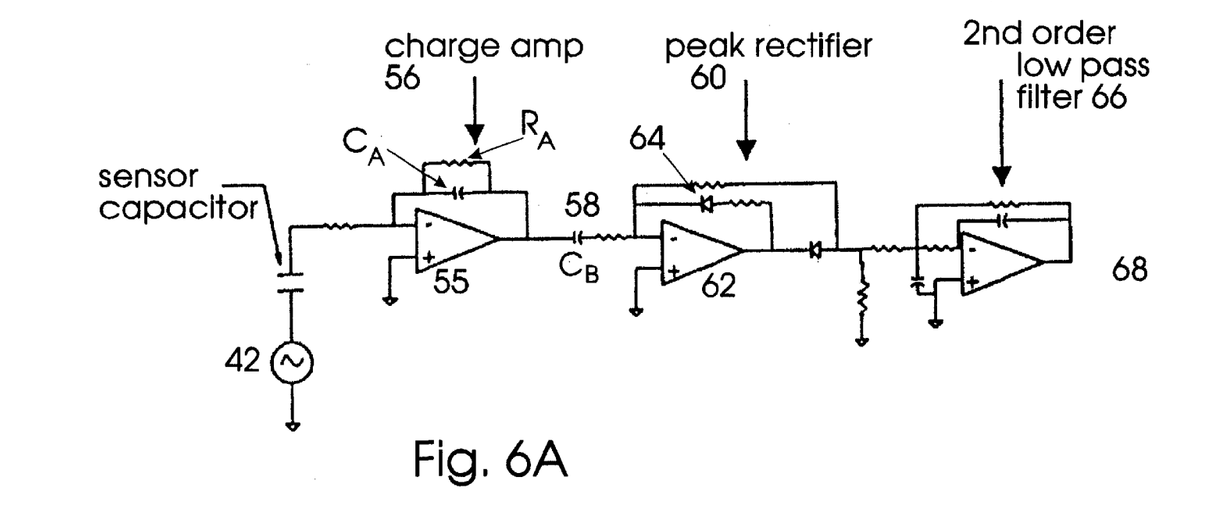
FIG. 6A shows a block diagram of the electronics of the invention.

Circuit 50 serves to amplify and filter the signal from sensor 20 while maintaining both ac and dc coupling. As shown in FIG. 6A, the first stage of each analog circuit 50-x is a charge amplifier 56 that converts the sensor current to a voltage and amplifies that signal. As is well known in the art, charge amplifier 56 is preferably an op-amp 55 with the non-inverting input terminal grounded, inverting input terminal connected to the sensor capacitor, and negative feedback elements $R_A$ and $C_A$. At frequencies above the cutoff, $f_c(R_A C_A)$, and below the roll-off of the op-amp (2 MHz) the circuit acts as an amplifier with response $$V_{out}(\omega) = -\frac{j\omega C_{sen} R_A}{1 + j\omega C_A R_A} V_{osc}(\omega) \qquad (3)$$

where $$f_c(R_A C_A) = \frac{1}{2\pi R_A C_A} \qquad (4)$$

$C_{sen}$ is the sensor capacitance, $\omega=2\pi f_{osc}$, and $V_{osc}(t)$ is the oscillator output. This result assumes that the sensor capacitance changes slowly relative to the oscillator frequency. As an aside, it is clear from Eq. (3) and Fourier transform theory that $V_{out}$ approaches the derivative of $V_{in}$ at frequencies below $f_c$, implying that caution must be taken in the choice of values of $f_{osc}$, $R_A$, and $C_A$ to avoid the frequency region below the cut-off frequency. The classical charge amplifier does not include the parallel resistor $R_A$; however, the realizable circuit requires input DC bias current to the gate of the J-FET op-amp for stability. The value of $R_A$ is made as large as possible to approximate the performance of the classical charge amplifier and the gain in Eq. (3) approaches $C_{sen}/C_A$ in the limit as R→∞.

To maximize the gain of the charge amplifier while maintaining circuit stability, $C_A$ is chosen to be 2.2 pF. Smaller values are available, but parasitic capacitances generally dominate for such choices. Also, some op-amp circuits are not stable with gains much less than one and with less feedback capacitance. To reduce electromagnetic interference (EMI), $R_A$ is chosen so that the cutoff is below the oscillator frequency but well above 60 Hz. With $R_A$=22 MΩ, $f_c(R_A C_A)$=3300 Hz. Care must be taken not to saturate an amplifier stage due to input bias current passing through the large feedback resistor. J-FET input op-amps have extremely low bias current ($Z_{in}>10^{12}\Omega$) and alleviate this concern.

A simple RC high-pass filter 58, such as a series capacitor $C_B$, is connected to the output of charge amp 56. This filter blocks input bias offsets as well as low frequency noise, such as 60 Hz. The input resistance of the following stage 60 is 10 kΩ. A capacitor choice $C_B$ of 1 nF provides a cutoff of 16 kHz. Also, for very noisy environments, higher order filters could be made by cascading RC sections.

The output signal from high pass filter 58 is essentially an amplitude modulated (AM) sine wave with a carrier frequency of $f_{osc}$ and an AM signal that is an image of the cloth. A detector is used to remove the carrier and thereby extract the modulation signal. For a capacitance sensor operating in a noisy environment, the noise can either be removed before detection or in the detector itself. If the noise can be removed before detection, then the detector circuit can be an AM detector. If the noise must be removed in the detector, a synchronous detector can be used.

The precision peak rectifier 60 (also known as a "Super-Diode") is identical to the AM detector except that diode 64 is placed inside the feedback loop of an op-amp 62. This modification effectively reduces the turn-on voltage of the diode to zero, producing a realization of an ideal diode. Small signals are not cut out by the precision peak rectifier.

The output of rectifier 60 is connected to low-pass filter 66, which filter forms the average of the detector output, suppresses noise, and suppresses the oscillator feed-through. Filter 66 must suppress any significant noise in the frequency range of one half of the sampling rate utilized in subsequent A/D conversion. These could include electrical noise from the building, mechanical noise from the equipment, etc. For a synchronous detector circuit, the low-pass filter takes on the additional role of completing the band-pass function of the circuit. All low pass filters produce an averaging function, the frequency at which the average is updated being determined from the cutoff frequency of the filter. For example, a filter with a cutoff frequency $f_c$ of 1 kHz will respond to a change at its input with a time constant $\tau = \frac{1}{2}\pi f_c \approx 160 \mu s$. Thus, if the cutoff frequency of the low-pass filter is lowered, then the response of the filter is slowed.

The cutoff must be placed above the signal frequency of interest or else the filter will not be able to respond to the signal. For greige inspection, the signal frequency is approximately equal to the rate at which pick threads pass over the sensor, or between 5 and 20 Hz. The signal frequency is determined by the cloth style but is not a constant due to the impulse nature of cloth manufacture.

Figure 6B:
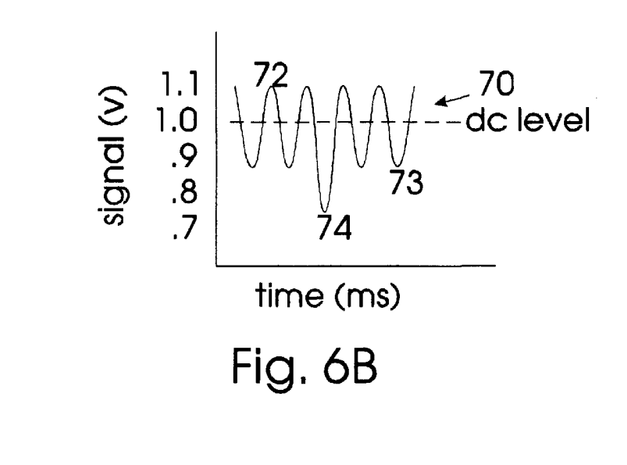
FIGS. 6B and 6C show output voltages for the electronics of FIG. 6A.
Figure 6C:
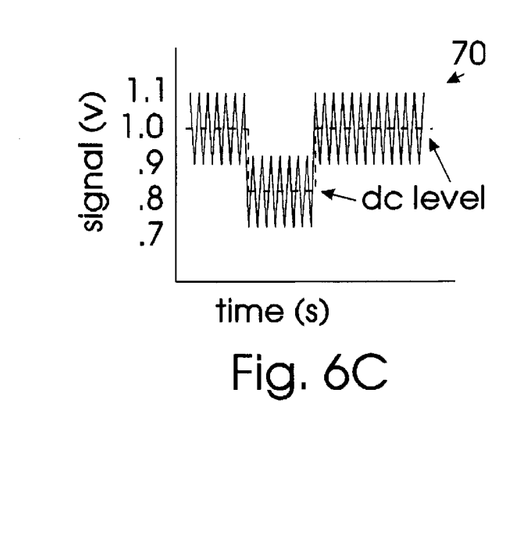

The output 68 of each filter 66 represents the change in capacitance of each capacitive sensor 22, 24 as a function of voltage. As shown in FIG. 6B, each peak 72 of the waveform 70 at output 68 represents a pick thread passing gap G of the sensor of FIG. 4, while each valley represents the space between threads. If a broken thread (as indicated by the dark arrow in FIG. 7) passes the sensor, the valley 74 is accentuated. In addition, the dc level of the signal 70 provides an indication of the number of warp threads passing each sensor element 24. As illustrated in FIG. 6C, if a warp thread is missing (as indicated by the white arrow in FIG. 7), the dc value of waveform 70 decreases.

For further processing, these analog signals are converted to digital signals by analog to digital (ADC) converter 70 and applied to microcontroller 80 where the signal anomalies are detected and recorded as discussed hereinafter.

Since each sensor 20-x provides a signal representing only a small portion of the width of web 8, the signal is converted to a digital signal and multiplexed for subsequent processing. The resolution of the ADC 52 in bits determines the precision and dynamic range of the digital information, with the precision of the conversion increasing with the number of ADC bits. At the same time, the dynamic range of the ADC also increases with the number of ADC bits. The dynamic range defines the measurability of both large and small signals in the same system, and it is given by the ratio of the largest measurable signal to the smallest measurable signal. This measure is particularly important in DC-coupled systems, such as disclosed herein, where the pick and warp signals are small changes on a large DC signal.

An implementation of ADC 52 utilized the Maxim MAX186DCPP, an internal 8-1 analog multiplexer with a maximum conversion time of 10 $\mu s$ and conversion to 12 bits.

The MAX186 ADC was configured for this system to operate on ±5 V supplies, use an external, adjustable voltage reference, and convert in unipolar mode. The external reference was generated from a potentiometer connected between analog ground and the positive supply. Thus, the input voltage range was tunable between the levels of 0V and 4.096V. A precision voltage reference diode could also be used in place of the potentiometer to eliminate sensitivity to power supply fluctuations.

If the web to be inspected is wider than sensor board 20, a number of boards 20 may be aligned with each board having its dedicated electronics as shown in FIG. 4 through A/D converter 52. The outputs of all such A/D converters 52 are then multiplexed as well known in the art and fed into microcontroller 54 for processing.

The details of the signal processing by processor 54 are not part of this invention. The system forms an image of the web from the sensed signals, analyzes the image, and determines the presence or absence of a defect. For greige goods, the system was designed to detect pick defects and warp defects, among others. The dark arrow in FIG. 7 points to a minor pick defect (a broken thread), while the white arrow points to a major warp defect (a missing thread). Since the system must provide 'real-time' indications of defects, the output of the processor is a report that is issued whenever a defect is detected and which includes the location, size, orientation, and contrast of the problem. This report is stored in a flash-memory which is downloaded by the control system for the loom. All of the reports for a given run may also be applied to grading software that assigns points for each defect based on a predetermined value system and provides a grade for the processed web.

Figure 8:
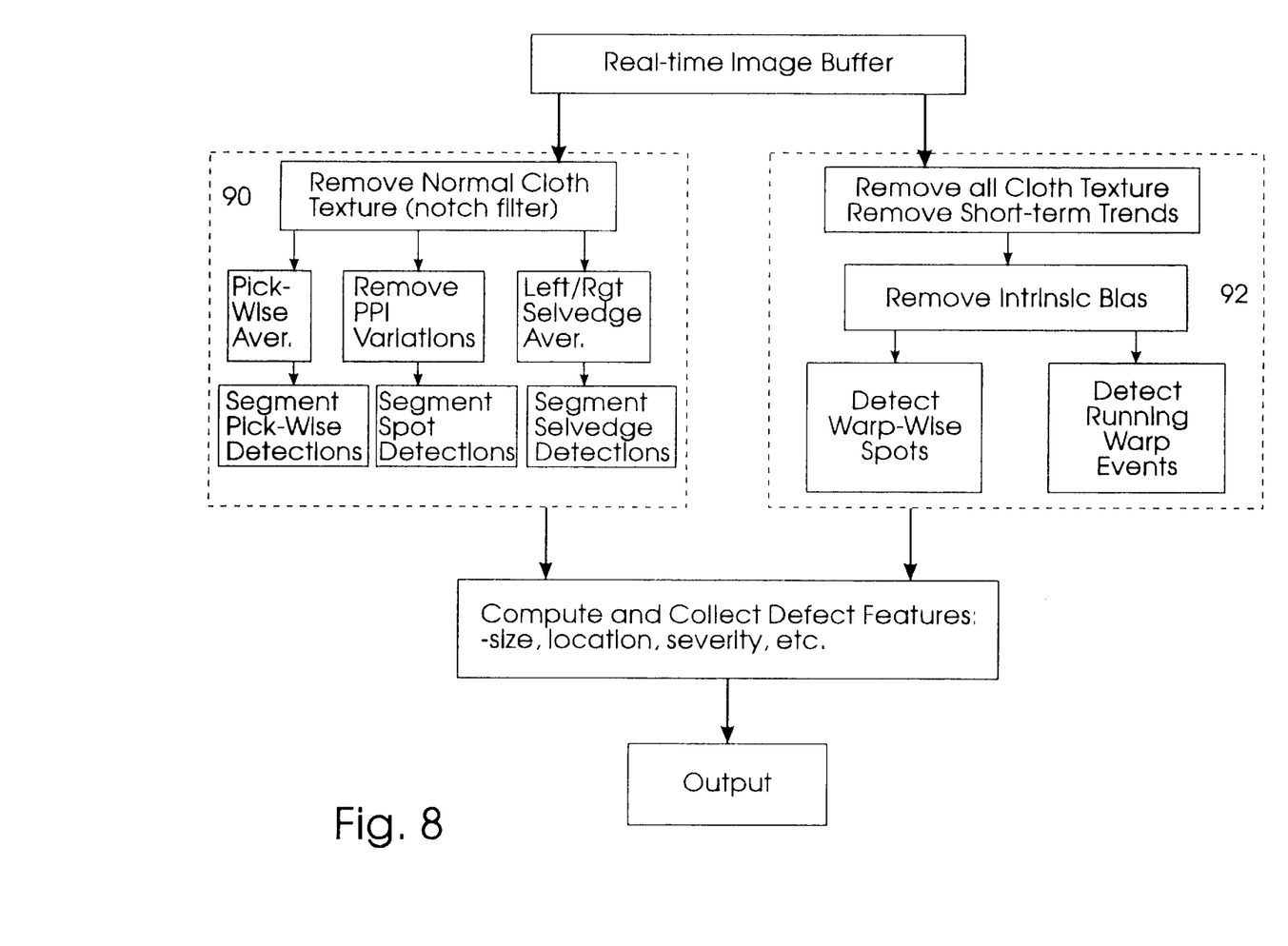
FIG. 8 describes the signal processing utilized with the invention.

The general algorithmic approach is shown in FIG. 8. The input to the processor is an image buffer that communicates directly with the sensor hardware. After all sensors have been scanned, they are processed as described below while subsequent scans are held in the buffer.

The primary algorithms operate as two separate real-time processes, as indicated by the dashed boxes in FIG. 8. The first process 90 encompasses pick and edge defects and operates on the detected ac-coupled signal of FIG. 6B. The pick lines are first enhanced by removing the dc signal and the image is filtered to remove normal cloth texture, leaving an enhanced representation of deviations from normal cloth. Additional processing is then applied to capture small defects.

An adaptive segmentation and thresholding technique determines whether or not the buffer contains a potential defect. The system 'learns' the statistics of 'good' cloth and compares that with the statistics of the measured cloth on a sensor-by-sensor basis. A binary image is built of for all the sensors (pixels) where a one represents a difference and a zero a match from the comparison. This image is segmented into regions to determine if there is a geometric pattern consistent with an identified defect. For example, the broken pick in FIG. 7 would be detected only by one sensor, where a missing pick thread would be detected by all pick sensors.

The second process 92 detects variations in warp-wise cloth bulk as a change in the dc level of the sensor output. Since, as shown in FIG. 7, the length of each sensor 24 is relatively large compared to each warp thread W, each sensor output represents an aggregate measurement on all the warp yarns passing that sensor. As shown in FIG. 6C, if a yarn (such as w10) is missing, then a relatively small decrease in dc level is observed. These fluctuations are compared with fluctuations measured from 'good' cloth. This algorithm must also account for non-cloth-induced dc variations, which may be caused by temperature, humidity, and web tension. Since these environmental changes effect all sensors, it may be compensated for by subtracting changes which affect many neighboring sensors from the signal being processed. By utilizing substantial averaging in the warp direction, very subtle warp variations may be detected.

The particular sizes and equipment discussed above are cited merely to illustrate a particular embodiment of this invention. It is contemplated that the use of the invention may involve components having different sizes and shapes as long as the principles disclosed herein are followed. For example, the system could be used on other flexible websthan cloth, as long as such webs have elongated parallel elements preferably arranged either parallel to the gap between transmit and receive electrodes, or perpendicular to that gap. In addition, while the invention is described using ac and dc to differentiate changes in these two groups of perpendicular elements, other electrical characteristics could also be utilized. It is intended that the scope of the invention be defined by the claims appended hereto.

What is claimed is:

1. A system comprising:
   a web support structure;
   a flexible web extending from a first end to a second end under longitudinal tension along a path;
   a capacitive sensor comprising a flexible electrically insulating substrate formed of a thin dielectric material having rigidly mounted thereon spaced, electrically conductive, transmit and receive electrodes;
   a sensor support for rigidly holding a portion of said flexible electrically insulating substrate in a curved position forming a convex side and an opposed concave side, the convex side holding said electrodes against said web with sufficient force to cause said path to be longer than the shortest distance between said first and second ends, said electrodes being adjacent said portion of said substrate; and
   means for moving said web relative to said sensor.

2. The system of claim 1 wherein said first and second ends are each defined by a web-bearing surface affixed to said web support structure and extending transverse to said path.

3. The system of claim 2 wherein said transmit and receive electrodes are mounted adjacent each other on the same side of said flexible electrically insulating substrate.

4. The system of claim 1 further comprising an electrically conductive and flexible second layer on the concave side of said flexible electrically insulating substrate.

5. The system of claim 4 further comprising a third layer of flexible electrically insulating material covering said electrodes and said convex side of said flexible electrically insulating substrate, and a flexible fourth layer of flexible electrically insulating material covering said second layer.

6. A flexible sensor comprising:
   a flexible circuit board having a flexible first layer of electrically insulating material having opposed sides, one of said sides having fastened thereto an electrically conductive and flexible electrode pattern containing a transmit electrode and an opposed receive electrode;
   structure holding said flexible circuit board in a curved position forming a convex side and an opposed concave side, the convex side having said electrode pattern and forming a bearing surface for an object to be sensed.

7. The flexible sensor of claim 6 further comprising an electrically conductive and flexible second layer on the other side of said flexible circuit board.

8. The flexible sensor of claim 7 further comprising a third layer of flexible electrically insulating material covering said electrically conductive pattern and said one side of said first layer, and a fourth layer of flexible electrically insulating material covering said second layer.

9. The flexible sensor of claim 8 wherein said electrically insulating material is a thin polyamide film.

10. The flexible sensor of claim 6 wherein said transmit electrode consists of a long rectangular pattern and said receive electrode consists of a plurality of shorter rectangular patterns aligned end-to-end with each other, each of said shorter patterns being parallel to and spaced across a gap from said long rectangular pattern.

11. The flexible sensor of claim 10 wherein said sensor further comprising an oscillator connected to apply an ac signal to said transmit electrode, and a plurality of output circuits, one of said output circuits being connected to each of said receive electrodes, each said output circuit producing an electrical signal representative of the capacitance between said transmit electrode and each receive electrode.

12. The flexible sensor of claim 11 wherein the electrical signal produced by each output circuit has a first electrical characteristic when a plurality of parallel elongated elements aligned parallel to said electrodes move across said gap; and a second electrical characteristic when a plurality of parallel elongated elements aligned perpendicular to said electrodes move across the receive electrode connected to said circuit.

13. The flexible sensor of claim 12 wherein said first electrical characteristic is alternating current and said second electrical characteristic is direct current.

14. The flexible sensor of claim 13 wherein each said output circuit comprises, in series, circuitry producing a sine wave at the frequency of said oscillator, said sine wave being modulated by a signal representative of the changes in capacitance across the gap; and a detector for removing the modulation from the sine wave, said modulation yielding said electrical signal.

15. The flexible sensor of claim 14 wherein said circuitry comprises a charge amplifier for producing a voltage representative of the current through each receive electrode; and a high pass filter.

16. The flexible sensor of claim 15 wherein said detector comprises a rectifier in series with a low pass filter.

17. The flexible sensor of claim 6 wherein said pattern further comprises a plurality of traces, one of said traces extending from each electrode to an edge of said circuit board.

18. The flexible array of claim 17 wherein all traces extending from receive electrodes have approximately the same impedance value.

19. The flexible sensor of claim 18 wherein all traces extending from receive electrodes have approximately the same length and width.

20. The flexible sensor of claim 6 wherein said structure holding said flexible circuit board comprises a rigid rod, wherein the concave side of said board is adjacent said rod.

21. The flexible sensor of claim 20 wherein said structure holding said flexible circuit board further comprise means for clamping said board to said rod.

22. The flexible sensor of claim 21 wherein said means for clamping comprises a fastener extending from adjacent one edge of said board to an opposite edge of said board, said edges and said fastener being on the opposite side of said rod from said bearing surface.

* * * * *